United States Patent [19]
Cheng et al.

[11] Patent Number: 5,955,551
[45] Date of Patent: Sep. 21, 1999

[54] POLYGLYCIDYL ETHERS OF SECONDARY ALCOHOLS, THEIR PREPARATION, AND CURABLE COMPOSITIONS CONTAINING THEM

[75] Inventors: Chi-Wen Frank Cheng, New City; Mark Bryant, Bedford Hills, both of N.Y.

[73] Assignee: Ciba Specialty Chemicals Corporation, Tarrytown, N.Y.

[21] Appl. No.: 08/907,285

[22] Filed: Aug. 6, 1997

Related U.S. Application Data

[60] Provisional application No. 06/023,469, Aug. 6, 1996.
[51] Int. Cl.[6] .................. C08G 59/04; C07D 303/24; C09D 163/00
[52] U.S. Cl. ............... 525/507; 528/88; 528/89; 528/90; 528/91; 528/92; 528/93; 528/94; 528/95; 528/97; 528/98; 549/517; 549/560; 428/413
[58] Field of Search .................. 427/386; 525/507; 528/88, 89, 90, 91, 92, 93, 94, 95, 97, 98; 549/517, 560; 428/413

[56] References Cited

U.S. PATENT DOCUMENTS

| | | | |
|---|---|---|---|
| 3,920,613 | 11/1975 | Freeman et al. | 260/67.6 |
| 4,074,008 | 2/1978 | Green | 428/418 |
| 4,284,574 | 8/1981 | Bagga | 260/348.43 |
| 4,468,508 | 8/1984 | Ito et al. | 525/507 |
| 4,539,347 | 9/1985 | DeGooyer | 523/404 |
| 4,737,553 | 4/1988 | Gannon et al. | 525/481 |
| 4,754,003 | 6/1988 | Monnier | 525/490 |
| 4,845,172 | 7/1989 | Brytus et al. | 525/481 |
| 4,857,567 | 8/1989 | Laugal et al. | 523/415 |
| 4,980,428 | 12/1990 | Liu et al. | 525/502 |
| 5,075,411 | 12/1991 | Ogawa et al. | 528/99 |
| 5,117,010 | 5/1992 | Cheng | 549/516 |
| 5,118,729 | 6/1992 | Piechocki | 523/404 |
| 5,128,491 | 7/1992 | Cheng | 549/516 |
| 5,239,093 | 8/1993 | Cheng | 549/517 |
| 5,356,691 | 10/1994 | Yamamoto et al. | 428/112 |

FOREIGN PATENT DOCUMENTS

| | | |
|---|---|---|
| 0022073 | 1/1981 | European Pat. Off. . |
| 0263067 | 4/1988 | European Pat. Off. . |
| 0552864 | 7/1993 | European Pat. Off. . |
| 2635929 | 3/1977 | Germany . |

OTHER PUBLICATIONS

Chem. Abst. 115: 282176.
B. Ellis, "Chemistry & Technology of Epoxy Resins", 1993, pp. 24–26.
Derwent Abst. 94–206516.
Lee and Neville, "Handbook of Epoxy Resins", MgGraw–Hill, Apr. 1967.

*Primary Examiner*—Frederick Krass
*Attorney, Agent, or Firm*—David R. Crichton

[57] ABSTRACT

The present invention relates to polyglycidyl ether compounds containing at least three mono- or divalent radicals A of the general formula

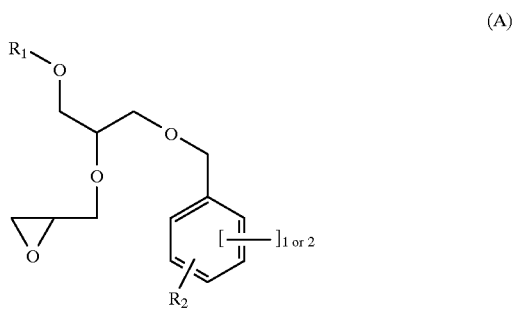

(A)

wherein $R_1$ represents (i) a straight chain or branched alkyl groups of 1 to 16 carbon atoms, which may be substituted by one to four chlorine or bromine atoms, or (ii) a straight chain or branched alkenyl group of 2 to 6 carbon atoms, which may be substituted by one to four chlorine or bromine atoms, or (iii) a phenyl or naphthyl group, optionally substituted in the ring or rings by one or two chlorine or bromine atoms or by one or two alkyl groups, each of 1 to 10 carbon atoms, and having in all from 7 to 30 carbon atoms, or (iv) a phenylalkyl or naphthylalkyl group, optionally substituted in the ring or rings by one or two chlorine or bromine atoms or by one or two alkyl groups, each of 1 to 10 carbon atoms, said phenylalkyl or naphthylalkyl group having in all from 7 to 30 carbon atoms, or (v) a mononuclear cycloalkyl group of 3 to 6 carbon atoms, or (vi) a mononuclear cycloalkylalkyl group of from 4 to 10 carbon atoms and $R_2$ represents hydrogen or a straight chain or branched alkyl groups of 1 to 9 carbon atoms. The invention further relates to processes for making and using the polyglycidyl ether compounds.

7 Claims, No Drawings

POLYGLYCIDYL ETHERS OF SECONDARY ALCOHOLS, THEIR PREPARATION, AND CURABLE COMPOSITIONS CONTAINING THEM

This application claims the benefit of U.S. Provisional Application No. 60/023,469, filed Aug. 6, 1996.

BACKGROUND OF THE INVENTION

It has now been found that certain new polyglycidyl ethers of secondary alcohols are curable resins having a low viscosity when compared, for example, to the widely used commercial resin EPN® 1180 having a viscosity of 20,000 centipoise at 52° C. The cured products made from the instant new compounds also show improved flexibility and solvent resistant. The resins according to the instant invention can be widely used especially in the fields of coating and encapsulation and specifically electric coating.

SUMMARY OF THE INVENTION

The present invention relates to polyglycidyl ether compounds containing at least three mono- or divalent radicals A of the general formula

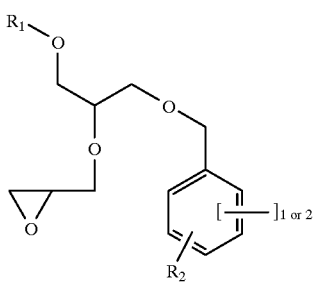
(A)

wherein $R_1$ represents (i) a straight chain or branched alkyl groups of 1 to 16 carbon atoms, which may be substituted by one to four chlorine or bromine atoms, or (ii) a straight chain or branched alkenyl group of 2 to 6 carbon atoms, which may be substituted by one to four chlorine or bromine atoms, or (iii) a phenyl or naphthyl group, optionally substituted in the ring or rings by one or two chlorine or bromine atoms or by one or two alkyl groups, each of 1 to 10 carbon atoms, and having in all from 7 to 30 carbon atoms, or (iv) a phenylalkyl or naphthylalkyl group, optionally substituted in the ring or rings by one or two chlorine or bromine atoms or by one or two alkyl groups, each of 1 to 10 carbon atoms, said phenylalkyl or naphthylalkyl group having in all from 7 to 30 carbon atoms, or (v) a mononuclear cycloalkyl group of 3 to 6 carbon atoms, or (vi) a mononuclear cycloalkylalkyl group of from 4 to 10 carbon atoms and $R_2$ represents hydrogen or a straight chain or branched alkyl groups of 1 to 9 carbon atoms.

The present invention further relates to polyglycidyl ether compounds containing at least three divalent radicals A as defined hereinabove having the following general formulas $$A—CH_2—[A—CH_2]_n—A \quad (I)$$

or $$(A)_3C—R_3 \quad (II)$$

or $$(A)_2CH—CH(A)_2 \quad (III)$$

wherein n is a number equal or greater 1, more preferably from 1 to 50, most preferably from 1 to 5, and $R_3$ is hydrogen or $CH_3$. In a preferred embodiment, $R_1$ represents straight chain or branched alkyl groups of 1 to 16 carbon atoms and $R_2$ is hydrogen. In a more preferred embodiment, the polyglycidyl ether compound may be represented by the general formula $$A—CH_2—[A—CH_2]_n—A \quad (I)$$

where n is a number from 1 to 5, $R_1$ is $C_4H_9$ and $R_2$ is hydrogen.

The present invention also relates to a process for the preparation of a polyglycidyl ether compound as described above containing at least three mono- or divalent radicals A as defined hereinabove comprising (a) reacting at least an equimolar amount, with respect to the glycidyl radicals of formula B, of an alcohol of the formula X $$R_1OH \quad (X)$$

wherein $R_1$ is defined hereinabove, with a polyglycidyl ether of a polyhydric phenol containing at least three mono- or divalent radicals B of the general formula

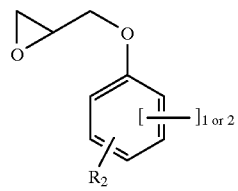

wherein $R_2$ is defined as hereinabove in the presence of a basic catalyst or a Lewis acid catalyst producing a poly-secondary alcohol; and (b1) reactng said poly-secondary alcohol with epichlorohydrin in the presence of an alkali and a phase transfer catalyst to produce said polyglycidyl ether compound containing at least three mono- or divalent radicals of the general formula A or (b2) reacting said poly-secondary alcohol with epichlorohydrin in the presence of a Lewis acid catalyst in a first stage and then in a second stage treating the poly(chlorohydrin) intermediate with an alkali to produce said polyglycidyl ether compound containing at least three mono- or divalent radicals of the general formula A.

In a still further embodiment, the present invention relates to a process for the preparation of a polyglycidyl ether compound as described above containing at least three mono- or divalent radicals A, as defined hereinbefore, comprising (a2) reacting a polyhydric phenol containing a radical $R_2$ and at least three OH-groups with a monoglycidyl ether of the formula XII

(XII)

wherein $R_1$ is defined hereinabove, optionally in the presence of a phase transfer catalyst producing a poly-secondary alcohol of the formula XIII containing at least three mono- or divalent radicals of the general formula C

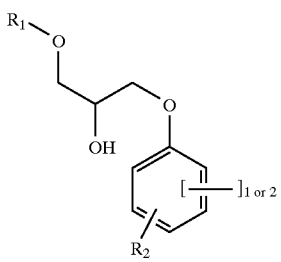

and (b1) reacting said poly-secondary alcohol with epichlorohydrin in the presence of an alkali and a phase transfer catalyst to produce said polyglycidyl ether compound containing at least three mono- or divalent radicals of the general formula A or (b2) reacting said poly-secondary alcohol with epichlorohydrin in the presence of a Lewis acid catalyst in a first stage and then in a second stage treating the poly(chlorohydrin) intermediate with an alkali to produce said polyglycidyl ether compound containing at least three mono- or divalent radicals of the general formula A.

DETAILED DESCRIPTION OF THE INVENTION

Accordingly, this invention provides polyglycidyl ether compounds containing at least three mono- or divalent radicals A of the general formula

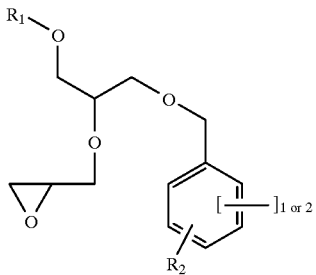
(A)

where $R_1$ represents (i) a straight chain or branched alkyl groups of 1 to 16 carbon atoms, which may be substituted by one to four chlorine or bromine atoms, or (ii) a straight chain or branched alkenyl group of 2 to 6 carbon atoms, which may be substituted by one to four chlorine or bromine atoms, or (iii) a phenyl or naphthyl group, optionally substituted in the ring or rings by one or two chlorine or bromine atoms or by one or two alkyl groups, each of 1 to 10 carbon atoms, and having in all from 7 to 30 carbon atoms, or (iv) a phenylalkyl or naphthylalkyl group, optionally substituted in the ring or rings by one or two chlorine or bromine atoms or by one or two alkyl groups, each of 1 to 10 carbon atoms, said phenylalkyl or naphthylalkyl group having in all from 7 to 30 carbon atoms, or (v) a mononuclear cycloalkyl group of 3 to 6 carbon atoms, or (vi) a mononuclear cycloalkylalkyl group of from 4 to 10 carbon atoms and $R_2$ represents hydrogen or a straight chain or branched alkyl group of 1 to 9 carbon atoms.

Preferably, the groups $R_1$ are the same and, in particular, each represents a straight chain or branched alkyl group of 1 to 14 carbon atoms, an allyl group, a cyclohexyl group, or a benzyl group. Particularly preferred is $R_1$ being $C_4H_9$.

Preferably, $R_2$ is hydrogen.

Preferably, the instant compounds are of the general formula $$A\text{—}CH_2\text{—}[A\text{—}CH_2]_n\text{—}A \qquad (I)$$

or $$(A)_3C\text{—}R_3 \qquad (II)$$

or $$(A)_2CH\text{—}CH(A)_2 \qquad (III)$$

where n is a number equal or greater 1 and $R_3$ is hydrogen or $CH_3$.

Compounds of formula (I) are preferred. In formula (I), the monovalent radicals A are preferably linked in the m or p position, relative to the ether group, to the $CH_2$-group. In formula (I), the $CH_2$-groups are preferably in the o or o and p position, relative to the ether group, on the divalent radical or radicals A.

Examples of compounds of formulae (I), (II) and (III) are:

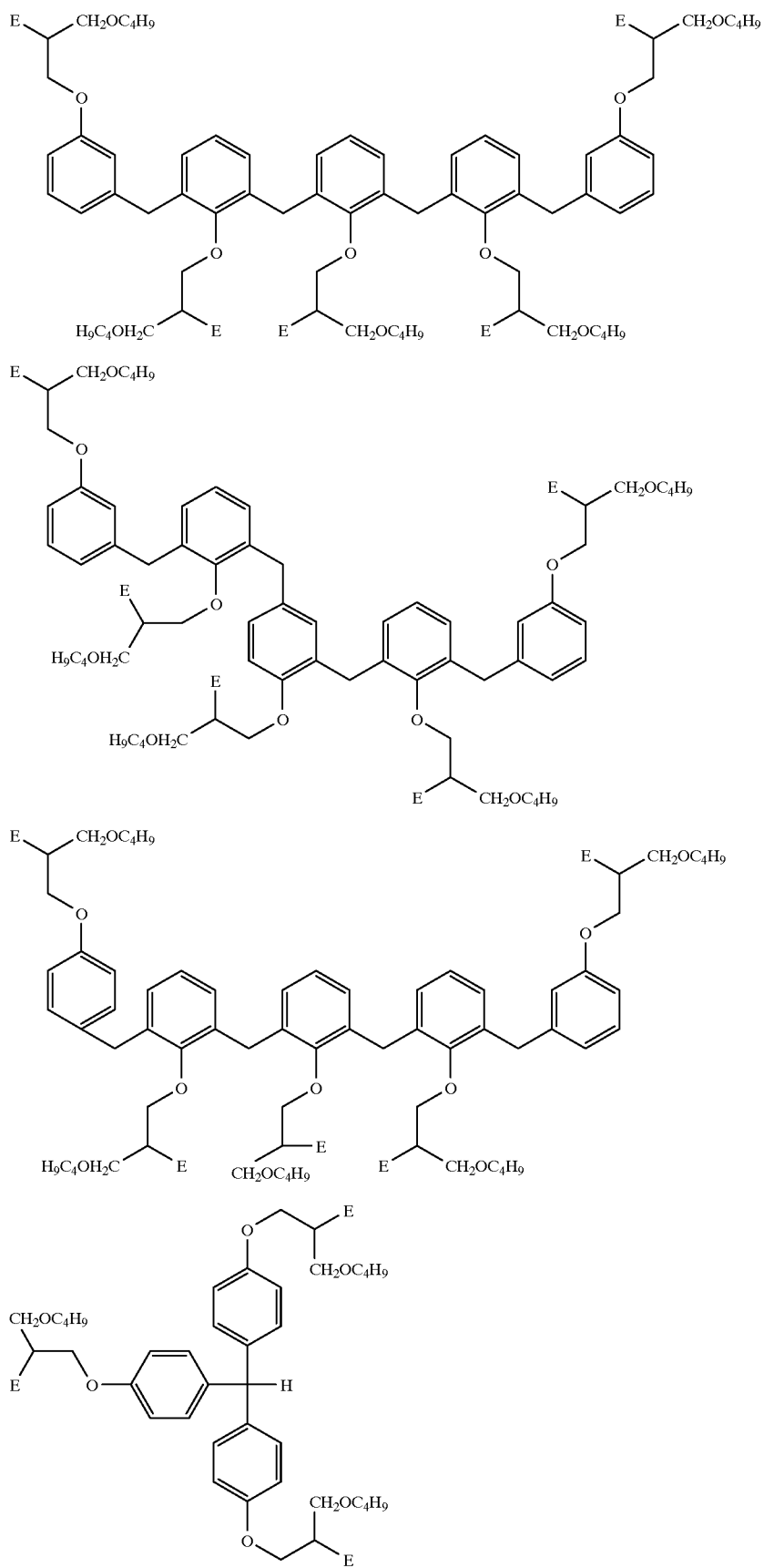

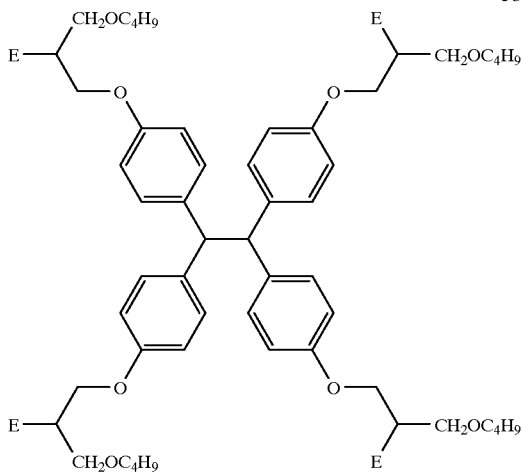

wherein E is the radical

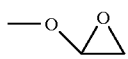

Further preferred compounds of formula (I) are those where n is a number between 1 and 50 and most preferred a number between 1 and 5.

Most preferred are compounds of formula (I) where n is a number from 1 to 5, $R_1$ is $C_4H_9$ and $R_2$ is hydrogen.

The invention also relates to a process for the preparation of a polyglycidyl ether compound containing at least three mono- or divalent radicals A, as defined hereinbefore, comprising (a) reacting at least an equimolar amount, with respect to the glycidyl radicals of formula B, of an alcohol of the formula X $R_1OH$           (X)

wherein $R_1$ is defined as hereinabove with a polyglycidyl ether of a polyhydric phenol containing at least three mono- or divalent radicals B of the general formula

wherein $R_2$ is defined as hereinabove
in the presence of a basic catalyst or a Lewis acid catalyst producing a poly-secondary alcohol; and (b1) reacting said poly-secondary alcohol with epichlorohydrin in the presence of an alkali and a phase transfer catalyst to produce said polyglycidyl ether compound containing at least three mono- or divalent radicals of the general formula A; or (b2) reacting said poly-secondary alcohol with epichlorohydrin in the presence of a Lewis acid catalyst in a first stage and then in a second stage treating the poly(chlorohydrin) intermediate with an alkali to produce said polyglycidyl ether compound containing at least three mono- or divalent radicals of the general formula A.

Preferably, alcohols wherein $R_1$ is an alkyl group of 1 to 14 carbon atoms, an allyl group, a cyclohexyl group, or a benzyl group are employed. Particularly preferred are alcohols wherein $R_1$ is an alkyl group of 1 to 14 carbon atoms.

Preferred poyglycidyl ethers of a polyhydric phenol are those wherein the monovalent radicals B are linked in the m or p position, relative to the ether group, and the divalent radical or radicals B are linked in the o or o and p position, relative to the ether group. Especially preferred polyglycidyl ethers of a polyhydric phenol are of the formula

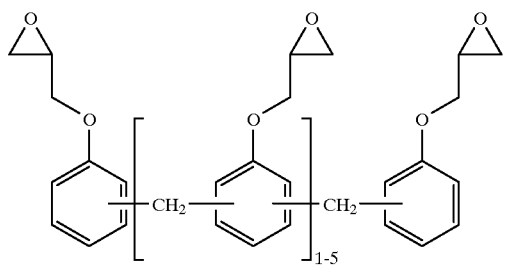

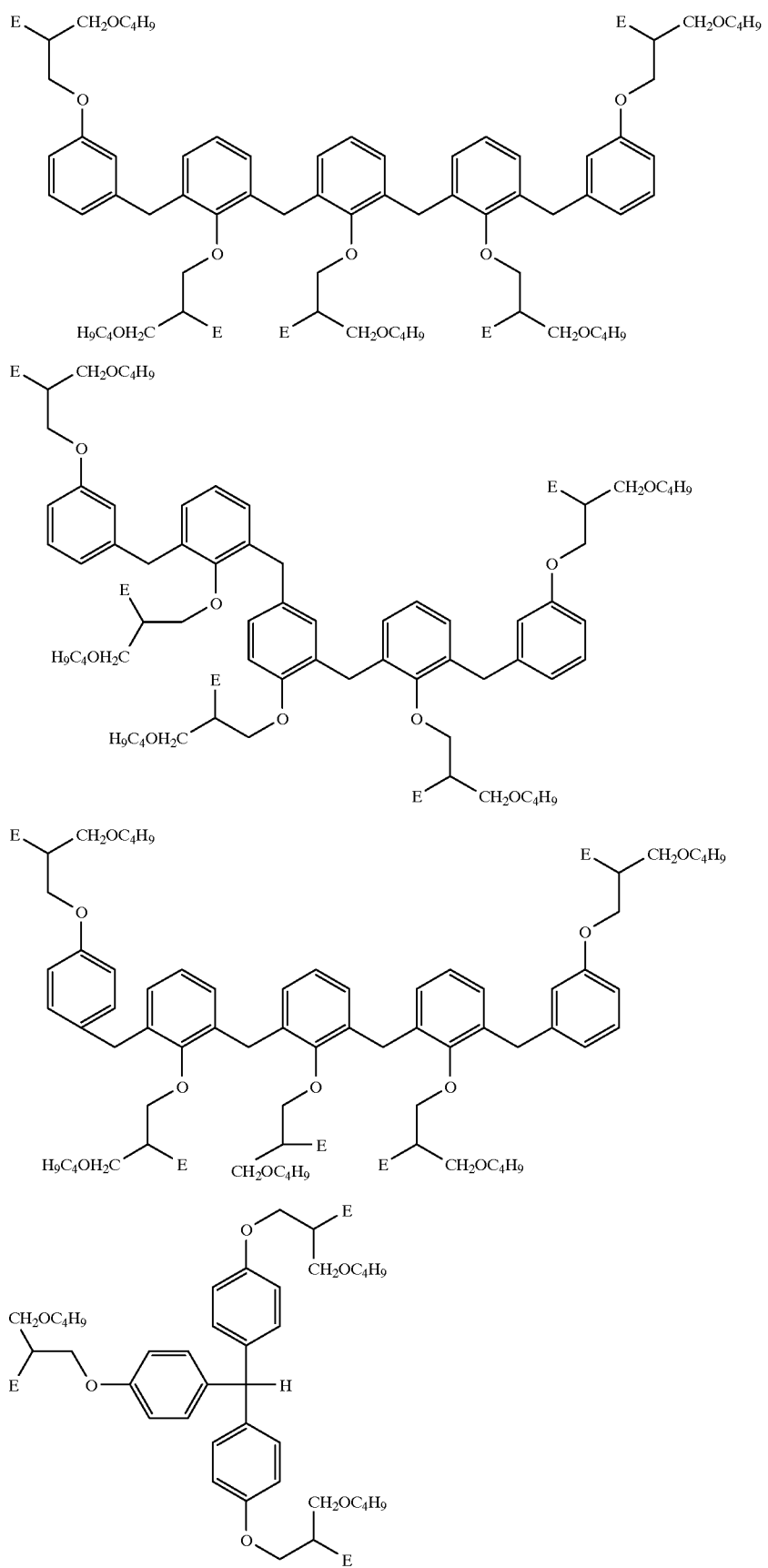

-continued

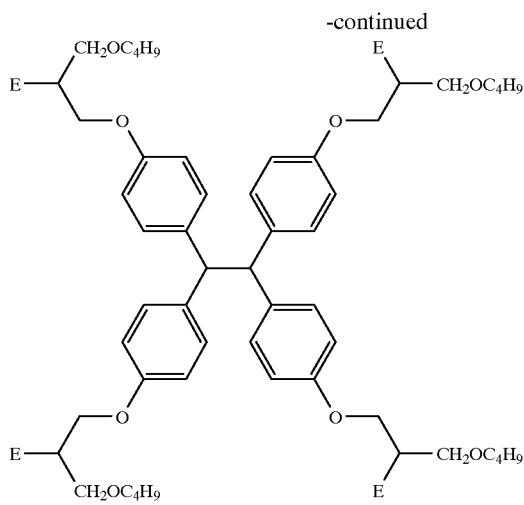

wherein E is the radical

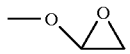

At least an equimolar amount, with respect to the glycidyl radicals of formula B, of the alcohol, preferably an equimolar amount to a threefold molar excess of the alcohol and most preferably a twofold molar excess of the alcohol is used.

Suitable basic catalysts include tertiary amine, quaternary ammonium base, alkali hydroxide and quaternary ammonium salt.

Suitable Lewis acid catalysts include boron trifluoride or a complex thereof, stannic chloride or a compound of the formula [MX], wherein M is a metal from Groups IB to VIIB or a metal or metalloid from Groups IIA to VA of the Periodic Chart of Elements or an ammonium ion and X is an anion selected from the group consisting of $BF_4^-$, $PF_6^-$, $AsF_6^-$, $AlF_4^-$, $TiF_6^{2-}$, $SiF_6^{2-}$, and $ZrF_6^{2-}$. A preferred catalyst is $BF_3$-etherate or $BF_3.2H_2O$. Preferred catalysts of the formula [MX] are those wherein M is a metal selected from the group consisting of copper, zinc, iron, magnesium, silver and calcium or a metalloid such as tin or arsenic or an ammonium ion and X is $BF_4^-$, $SiF_6^{2-}$ or $PF_6^-$. Particularly preferred compounds are $Sn(BF_4)_2$, $Fe(BF4)_2$, $Ca(BF_4)_2$, $Zn(BF_4)_2$, $Mg(BF_4)_2$, $Cu(BF_4)_2$, $NH_2BF_4$, $MgSiF_6$ and $AgPF_6$. Most particularly preferred are $Sn(BF_4)_2$, $Fe(BF_4)_2$, $Ca(BF_4)_2$, $Zn(BF_4)_2$, $Mg(BF_4)_2$, $Cu(BF4)2$, $NH_4BF_4$ and $AgPF_6$.

The reaction of the alcohol with the polyglycidyl ether of a polyhydric phenol is effected by heating the reactants at a temperature in the range of about 50 to 130° C., preferably about 70 to about 120° C., and most preferably about 90 to about 110° C., without solvent.

In the preparation of the polyglycidyl ether compound containing at least three mono- or divalent radicals of the general formula A, the residual alcohol remaining after completion of step (a) is conveniently removed by distillation.

The poly-secondary alcohol can then be reacted in step (b1) with an equimolar amount to an eightfold excess, with respect to the secondary alcohol groups, preferably, a threefold excess to a sixfold excess, most preferably a fivefold excess of epichlorohydrin in the presence of an equimolar amount to a 50% excess, with respect to the secondary alcohol groups, preferably an equimolar amount to a 10% excess of an alkali and in the presence of a phase transfer catalyst at a temperature in the range of about 30 to 90° C., preferably about 35 to about 75° C., and most preferably about 40 to about 65° C.

The poly-secondary alcohol can, alternatively, then be reacted in step (b2) with an equimolar amount to a fivefold excess, with respect to the secondary alcohol groups, preferably, an equimolar amount to a 50% excess, of epichlorohydrin in the presence of a Lewis acid catalyst at a temperature in the range of about 30 to 90° C., preferably about 35 to about 75° C., and most preferably about 40 to about 65° C.

In both methods (b1 or b2) the reaction may be carried out in the presence of a solvent such as a hydrocarbon, an ether, or a ketone, but use of an excess of epichlorohydrin as the solvent is preferred.

The reaction is typically conducted at a pressure of 70 to 260 torr in order to maintain a vigorous water-epichlorohydrin azetropic reflux.

Suitable alkali include sodium hydroxide, potassium hydroxide, sodium carbonate, potassium carbonate or a mixture thereof. Sodium hydroxide is preferred.

Suitable phase transfer catalysts include tetra-alkylammonium halides such as methyltrioctylammonium chloride, methyltridecylammonium chloride or tetramethylammonium chloride or a tertiary amine or quaternary ammonium base such as benzyltrimethylammonium or a quaternary ammonium salt such as benzyltrimethylammonium chloride. Benzyltrimethylammonium chloride is preferred. The phase transfer catalyst is generally used in an amount of about 0.1 to about 5 wt %, preferably about 0.5 to about 2.0 wt % and most preferably about 1.0 to about 1.5 wt % based upon the total weight of the reactants.

Suitable Lewis acid catalysts include boron trifluoride or a complex thereof, or stannic chloride.

The invention further relates to a process for the preparation of a polyglycidyl ether compound containing at least three mono- or divalent radicals A, as defined hereinbefore, comprising (a2) reacting a polyhydric phenol containing a radical $R_2$ and at least three OH-groups with a monoglycidyl ether of the formula XII

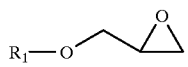
(XII)

wherein $R_1$ is defined hereinabove, optionally in the presence of a phase transfer catalyst producing a poly-secondary alcohol of the formula XIII containing at least three mono- or divalent radicals of the general formula C

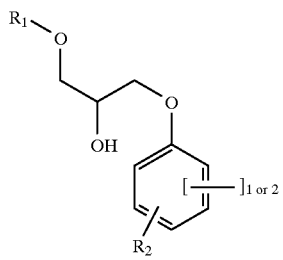
C and (b1) reacting said poly-secondary alcohol with epichlorohydrin in the presence of an alkali and a phase transfer catalyst to produce said polyglycidyl ether compound containing at least three mono- or divalent radicals of the general formula A; or (b2) reacting said poly-secondary alcohol with epichlorohydrin in the presence of a Lewis acid catalyst in a first stage and then in a second stage treating the poly(chlorohydrin) intermediate with an alkali to produce said polyglycidyl ether compound containing at least three mono- or divalent radicals of the general formula A.

Preferably, monoglycidylethers wherein $R_1$ is an alkyl group of 1 to 14 carbon atoms, an allyl group, a cyclohexyl group, or a benzyl group are employed. Particularly preferred are monoglycidylethers wherein $R_1$ is an alkyl group of 1 to 14 carbon atoms.

In the preparation of the polyglycidyl ether compound containing at least three mono- or divalent radicals of the general formula A, the monoglycidyl ether is reacted in step (a2) with about 0.2 mole to an equimolar amount, preferably, 0.6 to an equimolar amount, most preferably about 0.9 to an equimolar amount, with respect to the phenolic OH groups, of the polyhydric phenol in the presence of a phase transfer catalyst at a temperature in the range of about 30 to 90° C., preferably about 35 to about 75° C., and most preferably about 40 about 65° C.

Preferred polyhydric phenols are those wherein the monovalent phenol radicals are linked in the m or p position, relative to the OH group, and the divalent phenol radical or radicals B are linked in the o or o and p position, relative to the OH group. Especially preferred polyhydric phenols are of the formula

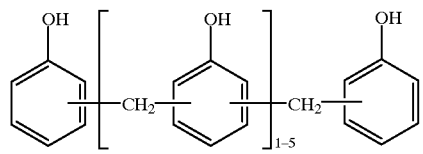

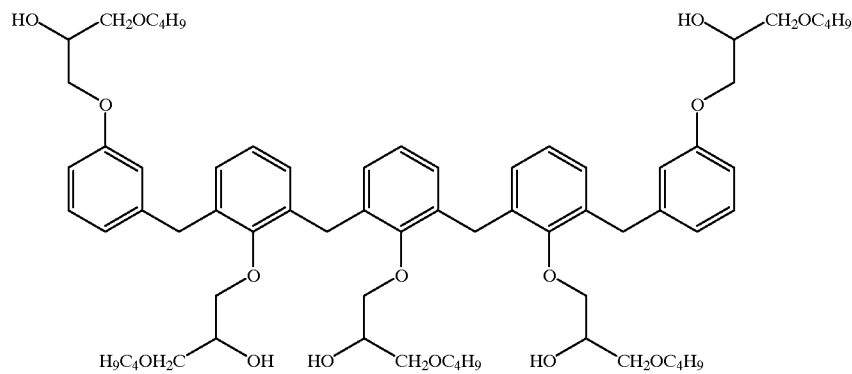

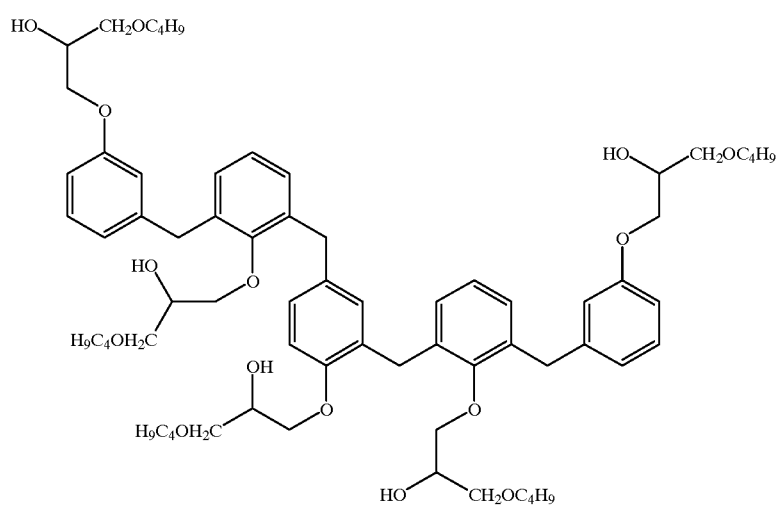
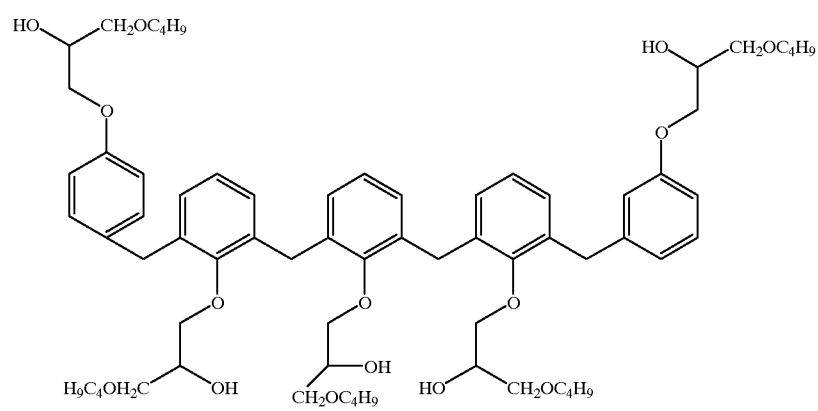
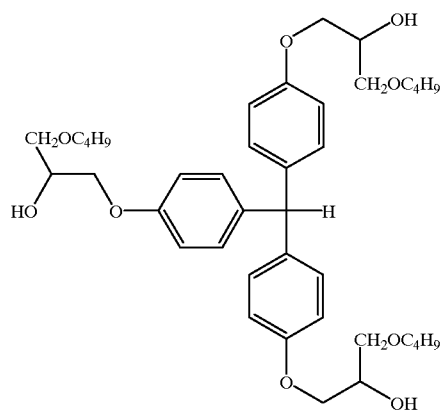

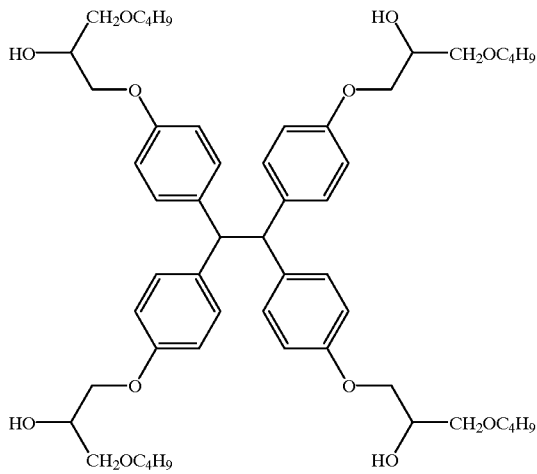

Suitable phase transfer catalysts include tetraalkylammonium halides such as methyltrioctylammonium chloride, methyltridecylammonium chloride or tetramethylammonium chloride or a tertiary amine or quaternary ammonium base such as benzyltrimethylammonium or a quaternary ammonium salt such as benzyltrimethylammonium chloride. Benzyltrimethylammonium chloride is preferred. The phase transfer catalyst is generally used in an amount of about 0.1 to about 5 wt %, preferably about 0.5 to about 2.0 wt % and most preferably about 1.0 to about 1.5 wt % based upon the total weight of the reactants.

The poly-secondary alcohol can then be reacted in step (b1) with an equimolar amount to an eight-fold excess, with respect to the secondary alcohol groups, preferably, a three-fold excess to a six-fold excess, most preferably a fivefold excess of epichlorohydrin in the presence of an equimolar amount to a 50% excess, with respect to the secondary alcohol groups, preferably an equimolar amount to a 10% excess of an alkali and in the presence of a phase transfer catalyst at a temperature in the range of about 30 to 90° C., preferably about 35 to about 75° C., and most preferably about 40 to about 65° C.

The poly-secondary alcohol can, alternatively, then be reacted in step (b2) with an equimolar amount to a fivefold excess, with respect to the secondary alcohol groups, preferably, an equimolar amount to a 50% excess, of epichlorohydrin in the presence of a Lewis acid catalyst at a temperature in the range of about 30 to 90° C., preferably about 35 to about 75° C., and most preferably about 40 to about 65° C.

In both methods (b1 or b2) the reaction may be carried out in the presence of a solvent such as a hydrocarbon, an ether, or a ketone, but use of an excess of epichlorohydrin as the solvent is preferred.

The reaction is typically conducted at a pressure of 70 to 260 torr in order to maintain a vigorous water-epichlorohydrin azetropic reflux.

Suitable alkali include sodium hydroxide, potassium hydroxide, sodium carbonate, potassium carbonate or a mixture thereof. Sodium hydroxide is preferred.

Suitable phase transfer catalysts include tetraalkylammonium halides such as methyltrioctylammonium chloride, methyltridecylammonium chloride or tetramethylammonium chloride or a tertiary amine or quaternary ammonium base such as benzyltrimethylammonium or a quaternary ammonium salt such as benzyltrimethylammonium chloride. Benzyltrimethylammonium chloride is preferred. The phase transfer catalyst is generally used in an amount of about 0.1 to about 5 wt %, preferably about 0.5 to about 2.0 wt % and most preferably about 1.0 to about 1.5 wt % based upon the total weight of the reactants.

Suitable Lewis acid catalysts include boron trifluoride or a complex thereof, or stannic chloride.

The polyglycidyl ether compounds of the present invention can be cured, i.e., hardened, with substances used as curing agents for epoxide resins to form insoluble, infusible products having valuable technical properties. If desired, the polyglycidyl ethers of the present invention may be cured in the presence of other epoxide resins. There are accordingly further provided curable compositions comprising a polyglycidyl ether compound and a curing agent therefor and, optionally, another epoxide resin.

As examples of curing agents may be mentioned those conveniently employed as curing agents for epoxide resins, including aliphatic, cycloaliphatic, aromatic, and heterocyclic amines such as m- and p-phenylenediamine, bis(4-aminophenyl)methane, anilineformaldehyde resins, bis(4-aminophenyl) sulphone, ethylenediamine, propane-1,2-diamine, propane-1,3-diamine, N,N-diethylethylenediamine, hexamethylenediamine, diethylenetriamine, triethylenetetramine, tetraethylenepentamine, N-(2-hydroxyethyl)-, N-(2-hydroxypropyl)-, and N-(2-cyanoethyl)-diethylenetriamine, 2, 2,4-trimethylhexane-1,6-diamine, 2,3,3-trimethylhexane-1,6diamine, m-xylylenediamine, N,N-dimethyl- and N,N-diethylpropane-1,3-diamine, ethanolamine, bis(4-aminocyclohexyl)methane, 2,2-bis(4-aminocyclohexyl) propane, 2,2-bis(4-amino-3 -methylcyclohexyl)propane, 3aminomethyl-3,5,5-trimethylcyclohexylamine (isophoronediamine), and N-(2-aminoethyl)piperazine; dicyandiamide, polyaminoamides, e.g., those prepared from aliphatic polyamines and dimerised or trimerised unsaturated fatty acids; adducts of amines with stoichiometric deficits of polyepoxides such as a diglycidyl ether; isocyanates and isothiocyanates; polyhydric phenols, e.g., resorcinol, hydroquinone, 2,2-bis(4-hydroxyphenyl) propane, phenol-aldehyde resins, and oil-modified phenol-aldehyde resins, phosphoric acid; polythiols such as the "Thiokols" ("Thiokol" is a registered trademark); and polycarboxylic acids and their anhydrides, e.g. phthalic anhydride, tetrahydrophthalic anhydride, methylendomethylenetetrahydrophthalic anhydride, nonenylsuccinic anhydride, dodecenylsuccinic anhydride, hexahydrophthalic anhydride, hexachloroendomethylenetetrahydrophthalic anhydride and endomethylenetetrahydrophthalic anhydride and their mixtures, maleic anhydride, succinic anhydride, pyromellitic acid dianhydride, benzophenone-3,3',4,4'-tetracarboxylic acid dianhydride, polysebacic anhydride, polyazelaic anhydride, the acids corresponding to the aforementioned anhydrides, and also isophthalic acid, terephthalic acid, citric acid, and mellitic acid. Particularly preferred polycarboxylic acid or anhydride curing agents are those which, in admixture if necessary, are liquid at temperatures below 60° C. There may also be used catalytic polymerizing agents, such as tertiary amines (for example 2,4,6tris(dimethylaminoethyl)phenol and other Mannich bases, N-benzyldimethylamine, and triethanolamine); alkali metal alkoxides of alcohols (for example, the sodium alcoholate of 2,4-dihydroxy-3-hydroxymethylpentane), stannous salts of alkanoic acids (for example, stannous octanoate), Friedel-Crafts catalysts such as boron trifluoride and its complexes; and chelates formed by reaction of boron trifluoride, with e.g., 1,3diketones.

In conjunction with the curing agents there may also be used appropriate accelerators. When poly(aminoamides), dicyandiamides, polythiols, or polycarboxylic acid anhydrides are employed for curing, tertiary amines or their salts, quaternary ammonium compounds or alkali metal alkoxides can serve as accelerators. Examples of specific accelerators are N-benzyldimethylamine, 2,4,6tris (dimethylaminomethyl)phenol, imidazoles, and triamylammonium phenoxide.

Other accelerators which may be used include metal nitrates, particularly magnesium nitrate and manganese nitrate, fluorinated and chlorinated carboxylic acids and their salts, such as magnesium trifluoroacetate, sodium trifluoroacetate, magnesium trichloroacetate, and sodium trichloroacetate, trifluoromethanesulphonic acid and its salts, such as the manganese, zinc, magnesium, nickel, and cobalt salts, and magnesium perchlorate and calcium perchlorate.

An effective amount of the curing agent is employed. The proportion will depend on the chemical nature of the curing agent and the properties sought of the curable composition and its cured product; the optimum proportion can readily be determined by methods familiar to those skilled in the art. By way of illustration, however, when the curing agent is an amine there will normally be used from about 0.75 to 1.25 amino-hydrogen equivalents of the amine per 1,2-epoxy equivalent of the epoxide resin. When polycarboxylic acids or their anhydrides are used, usually from about 0.4 to 1.1 carboxylic acid, or carboxylic acid anhydride, equivalents are taken per 1,2-epoxy equivalent, while, with polyhydric phenols about 0.75 to 1.25 phenolic hydroxy equivalents of the curing agent per 1,2-epoxy equivalent are employed. Generally, from 1 to 40 parts by weight of a catalytic polymerizing agent are used per 100 parts by weight of the epoxide resin.

Curing can be carried out, depending on the nature of the curing agent, at room temperature (18° to 25° C.) or at higher temperatures (500 to 180° C., for example).

If desired, curing or hardening can be carried out in two stages, for example by interrupting the curing reaction or, if a curing agent requiring an elevated temperature for complete curing is used, by only partially curing at a lower temperature, to give a still fusible and soluble, curable precondensate or "B-stage" product, for use in making molding powders, sinter-coating powders, or prepregs in a manner known per se.

As already indicated, the compounds of this invention may be used with conventional epoxide resins.

In the usual methods of manufacturing many epoxide resins, mixtures of compounds of differing molecular weight are obtained, these mixtures ordinarily containing a proportion of compounds whose epoxide groups have undergone partial hydrolysis or in which epoxidation has not proceeded to completion. The average number of 1,2-epoxide groups per molecule of an epoxide resin need not be at least 2 and need not be integral; it is generally a fractional number, but must in any case be greater than 1.0.

Of the epoxide resins which may be used in admixture with the polyglycidyl ether compound the more suitable are those wherein the epoxide groups are also terminal, i.e., of formula

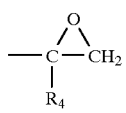

where $R_4$ denotes a hydrogen atom or a methyl group, and especially those where the groups are present as glycidyl or β-methylglycidyl groups directly attached to an atom of oxygen, nitrogen, or sulphur. Such resins include polyglycidyl and poly(β-methylglycidyl) esters obtainable by the reaction of a substance containing two or more carboxylic acid groups per molecule with epichlorohydrin, glycerol dichlorohydrin, or β-methylepichlorohydrin in the presence of alkali. The polyglycidyl esters may be derived from aliphatic carboxylic acids, e.g. oxalic acid, succinic add, adipic acid, sebacic acid, or dimerised or trimerised linoleic acid, from cycloaliphatic carboxylic acids such as hexahydrophthalic, 4-methylhexahydrophthalic, tetrahydrophthalic, and 4-methyltetrahydrophthalic acid, or from aromatic carboxylic acids such as phthalic acid, isophthalic acid, and terephthalic acid.

Other epoxide resins which may be used include polyglycidyl and poly(β-methylglycidyl) ethers obtainable by the reaction of substances containing per molecule, two or more alcoholic hydroxy groups, or two or more phenolic hydroxy groups, with epichlorohydrin, glycerol dichlorohydrin, or β-methylepichlorohydrin, under alkaline conditions or, alternatively, in the presence of an acidic catalyst with subsequent treatment with alkali. Such polyglycidyl ethers may be derived from aliphatic alcohols, for example, ethylene glycol and poly(oxyethylene)glycols such as diethylene glycol and triethylene glycol, propylene glycol and poly(oxypropylene) glycols, propane-1,3-diol, butane-1,4-diol, pentane-1,5-diol, hexane-1,6-diol, hexane-2,4,6-triol, glycerol, 1,1,1-trimethylolpropane, and pentaerythritol; from cycloaliphatic alcohols, such as quinitol, 1,1-bis (hydroxymethyl)cyclohex-3-ene, bis(4-hydroxycyclohexyl) methane, and 2,2-bis(4-hydroxycyclohexyl)-propane; or from alcohols containing aromatic nuclei, such as N,N-bis-(2-hydroxyethyl)aniline and 4,4'-bis(2-hydroxyethylamino) diphenylmethane. Preferably the polyglycidyl ethers are derived from substances containing two or more phenolic hydroxy groups per molecule, for example, resorcinol, catechol, hydroquinone, bis(4-hydroxyphenyl)methane, 1,1, 2,2-tetrakis(4-hydroxyphenyl)ethane, 4,4'-dihydroxydiphenyl, bis(4-hydroxyphenyl)sulphone, and especially, phenol-formaldehyde or cresol-formaldehyde novolac resins, 2,2-bis(4-hydroxyphenyl)propane (otherwise known as bisphenol A), and 2,2-bis(3,5-dibromo-4-hydroxyphenyl)-propane.

There may further be employed poly(N-glycidyl) compounds, such as are, for example, obtained by the dehydrochlorination of the reaction products of epichlorohydrin and amines containing at least two hydrogen atoms directly attached to nitrogen, such as aniline, n-butylamine, bis(4-aminophenyl)methane, bis(4-aminophenyl) sulphone, and bis(4-methylaminophenyl)methane. Other poly(N-glycidyl) compounds that may be used include triglycidyl isocyanurate, N,N'-diglycidyl derivatives of cyclic alkylene ureas such as ethyleneurea and 1,3-propyleneurea, and N,N'-diglycidyl derivatives of hydantoins such as 5,5-dimethylhydantoin.

Epoxide resins obtained by the epoxidation of cyclic and acrylic polyolefins may also be employed, such as vinylcyclohexene dioxide, limonene dioxide, dicyclopentadiene dioxide, 3,4-epoxydihydrodicyclopentadienyl glycidyl ether, the bis(3,4-epoxydihydrodicyclopentadienyl) ether of ethylene glycol, 3,4-epoxycyclohexylmethyl 3,4'-epoxycyclohexanecarboxylate and its 6,6'-dimethyl derivative, the bis(3,4-epoxycyclohexanecarboxylate) of ethylene glycol, the acetal formed between 3,4-epoxycyclohexanecarboxyaldehyde and 1,1-bis (hydroxymethyl)-3,4-epoxycyclohexane, bis(2, 3epoxycyclopentyl)ether, and epoxidized butadiene or copolymers of butadiene with ethylenic compounds such as styrene and vinyl acetate.

Especially suitable epoxide resins for mixing with the polyglycidyl ether compounds of the present invention are polyglycidyl ethers of 2,2-bis(4-hydroxyphenyl)propane or of a novolac from phenol (which may be substituted in the ring by a chlorine atom or an alkyl group of from 1 to 4 carbon atoms) and formaldehyde and having an epoxide content of at least 1.0 1,2-epoxide equivalent per kilogram.

The compositions of the invention may further contain plasticisers such as dibutyl phthalate, dioctyl phthalate, or tricresyl phosphate, inert diluents, and so-called reactive diluents, such as diglycidyl formal and especially monoepoxides such as butyl glycidyl ether, iso-octyl glycidyl ether, phenyl glycidyl ether, styrene oxide, glycidyl acrylate, glycidyl methacrylate, and glycidyl esters of synthetic, highly branched, predominantly tertiary, aliphatic monocarboxylic acids. They may also contain additives such as fillers, reinforcing materials, coloring matter, flow control agents, flame retardants, and mould lubricants. Suitable extenders, fillers, and reinforcing materials include asbestos, asphalt, bitumen, glass fibers, textile fibers, carbon fibers, boron fibers, mica, alumina, gypsum, titania, chalk, quartz flour, cellulose, kaolin, ground dolomite, wollastonite, colloidal silica having a large specific surface such as that available under the registered trademark "Aerosil" clays modified by treatment with long chain amines (such as those available under the registered trademark "Bentone"), powdered poly (vinyl chloride), powdered polyolefin hydrocarbons, powdered cured aminoplasts, and metal powders such as aluminum or iron powder. Flame retardants such as antimony trioxide may also be incorporated.

In the examples, as in the remainder part of the description, percentages are given as weight percentages and ranges include the stated limits, unless otherwise noted.

EXAMPLES

Example 1: 1515 g of n-butanol and 4.68 g of $BF_3.2H_2O$ are charged into a three liter 4-neck round bottom flask equipped with a mechanical stirrer. Using a heat tape 900 g of GY 1180 (Epoxy Cresol Novolac; Ciba) are added over a period of three hours to the stirred solution which is kept at 110° C. The pot temperature is risen to 115° C. and maintained until the epoxy value is less than 0.001eq/100 g. The pot is cooled to 80° C. and 4.68 g of 50% NaOH (aqueous solution) are added. After stirring for 15 minutes, the excess n-butanol is distilled off under reduced pressure so that the pot temperature is below 110° C. After the residue is cooled to about 60° C., 1768.6 g of epichlorohydrin, followed by 25.2 g of 50% benzyltrimethylammonium chloride (aqueous solution), are added under vigorous stirring. The mixture is heated to 50–55° C. under vacuum of 70 torr with water-epichlorohydrin reflux. Over a period of two hours, 195 g of 50% NaOH (aqueous solution) are added during which the water-epichlorohydrin azeotrope is distilled into a Dean-Stark trap where the water is retained and the epichlorohydrin is returned to the reactor. The azeotropic removal of water is continued for another two hours. The product is washed three times with 300 g of water whereby between the first and second washing the pH of the solution is adjusted to 6 with 10% aqueous acetic acid. The excess epichlorohydrin is distilled off to dryness at reduced pressure (less than 5 torr) so that the pot temperature is below 150° C. It gives a light yellow liquid as the product (1450 grams, yield 87%). The analytical data are in accordance with the desired product having an epoxy value of 0.282 eq./100 g (WPE:355), and a viscosity of 24,000 cps at 25° C.

What is claimed is:

1. A polyglycidyl ether compound containing at least three mono- or divalent radicals A of the general formula

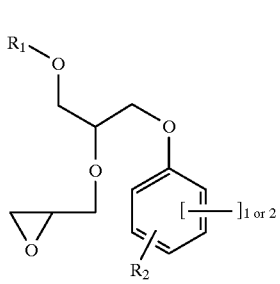

(A)

where
$R_1$ represents
(i) a straight chain or branched alkyl group of 1 to 16 carbon atoms, which may be substituted by one to four chlorine or bromine atoms, or
(ii) a straight chain or branched alkenyl group of 2 to 6 carbon atoms, which may be substituted by one to four chlorine or bromine atoms, or
(iii) a phenyl or naphthyl group, optionally substituted in the ring or rings by one or two chlorine or bromine atoms or by one or two alkyl groups, each of 1 to 1 0 carbon atoms, and having in all from 7 to 30 carbon atoms, or
(iv) a phenylalkyl or naphthylalkyl group, optionally substituted in the ring or rings by one or two chlorine or bromine atoms or by one or two alkyl groups, each of 1 to 10 carbon atoms, said phenylalkyl or naphthylalkyl group having in all from 7 to 30 carbon atoms, or
(v) a mononuclear cycloalkyl group of 3 to 6 carbon atoms, or
(vi) a mononuclear cycloalkylalkyl group of from 4 to 10 carbon atoms and $R_2$ represents hydrogen or a straight chain or branched alkyl group of 1 to 9 carbon atoms.

2. A compound according to claim 1 of the general formula

(I)

or $$(A)_3C-R_3 \qquad (II)$$

or $$(A)_2CH-CH(A)_2 \qquad (III)$$

where n is a number equal or greater 1 and $R_3$ is hydrogen or $CH_3$.

3. A compound according to claim 1 of the general formula $$A-CH_2-[A-CH_2]_n-A \qquad (I)$$

where n is a number from 1 to 50.

4. A compound according to claim 1 of the general formula $$A-CH_2-[A-CH_2]_n-A \qquad (I)$$

where n is a number from 1 to 5.

5. A compound according to claim 1 where $R_1$ represents straight chain or branched alkyl groups of 1 to 16 carbon atoms and $R_2$ is hydrogen.

6. A compound according to claim 1 of the general formula $$A-CH_2-[A-CH_2]_n A \qquad (I)$$

where n is a number from 1 to 5, $R_1$ is $C_4H_9$ and $R_2$ is hydrogen.

7. A process for preparing a substrate having a hardened coating comprising:

(a) combining a polyglycidyl ether compound according to claim 1 with a curing agent to produce a formulation; and (b) applying at least one layer of said formulation over said substrate.

* * * * *

UNITED STATES PATENT AND TRADEMARK OFFICE
CERTIFICATE OF CORRECTION

PATENT NO. : 5,955,551
DATED : SEPTEMBER 21, 1999
INVENTOR(S) : CHI-WEN FRANK CHENG ET AL.

It is certified that error appears in the above-identified patent and that said Letters Patent is hereby corrected as shown below:

On the title page, Section [60] should read:

-- Related U.S. Application Data

[60] Provisional application No. 60/023,469, Aug. 6, 1996. --.

Signed and Sealed this

Fifth Day of September, 2000

Attest:

Q. TODD DICKINSON

Attesting Officer

Director of Patents and Trademarks